United States Patent
Slatkin et al.

(10) Patent No.: US 9,375,587 B2
(45) Date of Patent: *Jun. 28, 2016

(54) LOW DOSE-RATE RADIATION FOR MEDICAL AND VETERINARY THERAPIES WITH THREE DIMENSIONALLY SHAPED PROFILES

(71) Applicant: MICROBEAM THERAPY, LLC, Redwood City, CA (US)

(72) Inventors: Daniel N. Slatkin, Essex, CT (US); Fred Harden Geisler, Chicago, IL (US)

(73) Assignee: MICROBEAM THEARPY, LLC., Redwood City, CA (US)

( * ) Notice: Subject to any disclaimer, the term of this patent is extended or adjusted under 35 U.S.C. 154(b) by 491 days.

This patent is subject to a terminal disclaimer.

(21) Appl. No.: 13/853,331

(22) Filed: Mar. 29, 2013

(65) Prior Publication Data

US 2013/0230145 A1 Sep. 5, 2013

Related U.S. Application Data

(63) Continuation-in-part of application No. 13/369,368, filed on Feb. 9, 2012, now Pat. No. 8,798,233.

(51) Int. Cl.
*A61N 5/10* (2006.01)
*G21K 1/02* (2006.01)

(52) U.S. Cl.
CPC ............ *A61N 5/1077* (2013.01); *A61N 5/1042* (2013.01); *G21K 1/02* (2013.01); *A61N 5/1049* (2013.01); *A61N 5/1068* (2013.01); *A61N 5/1078* (2013.01); *A61N 2005/1076* (2013.01); *A61N 2005/1091* (2013.01); *A61N 2005/1095* (2013.01); *A61N 2005/1097* (2013.01)

(58) Field of Classification Search
USPC ............. 378/65, 68, 147, 149, 150, 204, 205; 250/515.1
See application file for complete search history.

(56) References Cited

U.S. PATENT DOCUMENTS

| 4,868,843 A | 9/1989 | Nunan |
| 5,339,347 A | 8/1994 | Slatkin et al. |
| 5,771,270 A | 6/1998 | Archer |
| 8,798,233 B2 * | 8/2014 | Geisler ............... A61N 5/1042 378/147 |
| 2006/0176997 A1 | 8/2006 | Dilmanian et al. |
| 2013/0208865 A1 | 8/2013 | Geisler et al. |

OTHER PUBLICATIONS

Notification of Transmittal of the International Search Report and the Written Opinion of the International Searching Authority, or the Declaration issued in International Application No. PCT/US2014/032188, Oct. 8, 2014.

(Continued)

*Primary Examiner* — Jurie Yun
(74) *Attorney, Agent, or Firm* — Kramer & Amado P.C.

(57) ABSTRACT

Various embodiments relate to a method of performing microbeam radiation therapy (microbeam radiosurgery) for a subject, including: producing a high-energy radiation beam; shaping, attenuating, strengthening, hardening and/or otherwise appropriately modifying the high-energy radiation beam using a low-Z, high-Z, or variable-Z filter; passing the beam before or after it has been so modified through a collimator to produce high-dose regions alternating with low-dose regions; and irradiating the subject with the collimated beam so modified.

20 Claims, 5 Drawing Sheets

(56) References Cited

OTHER PUBLICATIONS

Ahunbay et al, "Direct Aperture Optimization-Based Intensity-Modulated Radiotherapy for Whole Breast Irradiation", Int. J. Radiation Oncology Biol. Phys., vol. 67, No. 4, 2007, pp. 1248-1258.
Slatkin et al, "Prospects for Microbeam Radiation Therapy of Brain Tumours in Children", Medical Department Brookhaven National Laboratory, 2008, p. 163.
W.P.M. Mayles, "Survey of the Availability and Use of Advanced Radiotherapy Technology in the UK", Clinical Oncology 22 (2010) pp. 636-642.
Beilajew, "The Effect of Strong Longitudinal Magnetic Fields on Dose Deposition from Electron and Photon Beams", Med. Phys. 20 (4), Jul./Aug. 1993, pp. 1171-1179.
Keall et al, "Electromagnetic-Guided Dynamic Multileaf Collimator Tracking Enables Motion Management for Intensity-Modulated ARC Therapy", Int. J. Radiation Oncology Biol. Phys., vol. 79, No. 1, 2011, pp. 312-320.
E. Brauer-Krisch et al, "Characterization of a Tungsten/Gas Multislit Collimator for Microbeam Radiation Therapy at the European Synchrotron Radiation Facility", Review of Scientific Instruments 76, 2005, 7 pages.
E. Brauer-Krisch et al, "Effects of Pulsed, Spatially Fractionated, Microscopic Synchrotron X-Ray Beams on Normal and Tumoral Brain Tissue", Mutation ReSearch 704/Reviews in Mutation Research, (2010), pp. 160-166.
E. Brauer-Krisch, "New Technology Enables High Precision Multislit Collimators for Microbeam Radiation Therapy", Review of Scientific Instruments 80, (2009), 6 pages.
Jian-Rong Dai et al, "Intensity-Modulation Radiotherapy Using Independent Collimators: An Algorithm Study", Med. Phys. 26 (12), 1999, pp. 2562-2570.
Hargrave et al, "Diffuse Brainstem Glioma in Children: Critical Review of Clinical Trials", http://oncology.thelancet.com, vol. 7, 2006, pp. 241-248.
Kalef-Ezra, "Health Physics Aspects in Treatment Rooms After 18-MV X-Ray Irradiations", Radiation Protection Dosimetry (2011), vol. 147, No. 1-2, pp. 1-6.
J.A. Laissue et al, "Prospects for Microbeam Radiation Therapy of Brain Tumours in Children to Reduce Neurological Sequelae", Developmental Medicine & Child Neurology, 2007, 49: 577-581.
Laissue et al, "The Weanling Piglet Cerebellum: A Surrogate for Tolerance to MRT (Microbeam Radiation Therapy) in Pediatric Neuro-Oncology", Proceedings of SPIE, vol. 4508 (2001), pp. 65-73.
Fan et al, "Intensity Modulation Under Geometrical Uncertainty: A Deconvolution Approach to Robust Fluence", Physics in Medicine and Biology 55 (2010), pp. 4029-4045.
Bert et al, "Motion in Radiotherapy: Particle Therapy", Physics in Medicine and Biology 56 (2011), pp. R113-R144.
Serduc et al, High-Precision Radiosurgical Dose Delivery by Interlaced Microbeam Arrays of High-Flux Low-Energy Synchrotron X-Rays, Synchrotron X-Ray Radiosurgery, vol. 5, issue 2, 2010, pp. 1-12.
Slatkin, "Uniaxial and Biaxial Irradiation Protocols for Microbeam Radiation Therapy", Institute of Physics Publishing, Phys. Med. Biol. 49 (2004), pp. N203-N204.
Slatkin, "Tetrahedral Irradiation Protocol for Microbeam Radiation Therapy", Institute of Physics Publishing, Phys. Med. Biol. 51 (2006), pp. N295-N297.
Cai et al, "Targeted Cancer Therapy with Tumor Necrosis Factor-Alpha", Biochemistry Insights, 2008, pp. 5-21.
Gonsalves et al, "Tunable Laser Plasma Accelerator Based on Longitudinal Density Tailoring", Nature Physics, 2011, pp. 1-5.
Esteban et al. "Reducing the Number of Segments in Unidirectional Segmentations of Fluence Matrices for Muitileaf Collimators in IMRT", M.Sc. Biomedical Engineering, 2010, pp. i-xii and 1-30.
International Search Report in corresponding PCT Application No. PCT/US2013/025267, issued on Apr. 3, 2013.

\* cited by examiner

LOW DOSE-RATE RADIATION FOR MEDICAL AND VETERINARY THERAPIES WITH THREE DIMENSIONALLY SHAPED PROFILES

This application is a continuation-in-part of U.S. patent application Ser. No. 13/369,368 filed on Feb. 9, 2012, which is hereby incorporated by reference for all purposes as if fully set forth herein.

TECHNICAL FIELD

Various exemplary embodiments disclosed herein relate generally to low-dose-rate radiation for medical and veterinary therapies with three-dimensionally shaped profiles. Such application is especially useful in treating various cancers and other tumors.

BACKGROUND

Cancer continues to be one of the foremost health problems. Conventional treatments such as surgery and chemotherapy have been extremely successful in certain cases; in other instances, much less so. Radiation therapy has also exhibited favorable results in many cases, while failing to be completely satisfactory and effective in all instances. It has been proposed that an alternative form of radiation therapy, known as microbeam radiation therapy (MRT) or microbeam radiosurgery (MBRS) may be used to treat certain tumors for which the conventional methods have been ineffective.

MRT or BMRS, hereafter designated MBRS, differs from conventional radiation therapy by employing multiple parallel fan beams of radiation with a narrow dimension or thickness that may be on the order of 10 to 200 micrometers. The thickness of the microbeams is dependent upon the capacity of tissue surrounding a beam path to support the recovery of the tissue injured by the beam. It has been found in experimental rodents that certain types of cells, notably endothelial cells lining blood vessels, but also oligodendroglial and other supporting cells, have the capacity to migrate over microscopic distances, infiltrating tissue damaged by radiation and reducing tissue necrosis in the beam path. In MBRS, sufficient unirradiated or minimally irradiated microscopic zones remain in the normal tissue but not in neoplastic tissue through which the microbeams pass to allow efficient repair of irradiation-damaged normal tissue. As a result, unidirectional MBRS is, fundamentally, greatly different from other forms of radiation therapy, while multidirectional, stereotactic MBRS is substantially different from other forms of stereotactic radiotherapy.

In conventional clinical forms of radiation therapy, including the radiosurgical techniques employing, steeotactically, multiple, slender, convergent beams of X-ray or gamma radiation, each beam is usually at least five hundred micrometers wide, so that the otherwise potential biological advantage of rapid repair by migrating or proliferating endothelial cells is minimal or nonexistent. Observations of the regeneration of blood vessels following MBRS indicate that endothelial cells cannot efficiently regenerate damaged blood vessels over distances on the order of more than 100 micrometers (µm). Thus, in view of this knowledge concerning radiation pathology of normal blood vessels, the skilled artisan may select a microbeam thickness as small as 20 µm but not more than 100 µm. Further, the microbeams may include substantially parallel, non-overlapping, planar beams with center-to-center spacing of from about 50 µm to about 500 µm. Also, the microbeam energies should be confined to the range from about 30 to several hundred keV, lest tissue penetration from lower energies be inadequate on one hand and lateral scattering of radiation from the high-dose in-beam path excessively increase the dose between microbeams, thereby obviating the microbeam normal-tissue-protective effect on the other hand. These microbeams result in a dosage profile with microscopically narrow (generally less than 100 µm wide) peaks and submillimeter-wide (generally less than a half-millimeter wide) valleys between them. The region between the peaks is called the valley region. The radiation dosage is large enough to render all cells in the targeted malignancy within the peak-zone slice non-clonogenic, but renders normal cells within the peak-zone slice proximal and distal to a targeted malignancy similarly non-clonogenic. The critical and novel therapeutic aspect of MBRS is that such damage proximal and distal to the malignancy is largely repaired by the influx of surviving progenitor cells from adjacent zones of low-dose normal tissue in the valleys. However, such damage to the targeted malignancy is therapeutically largely not repaired, putatively because the valley regions in the malignancy do not communicate well biologically with zones of cell loss in the nearby peak-dose regions of the same malignancy. Presumably, such lack of communication, especially among supporting cells of the malignancy, therapeutically impairs the viability and growth potential of the malignancy. The minimum radiation dosage in the valleys (i.e., the "nadir" valley dosage) must be just small enough to prevent clonogenically lethal damage to some necessary fraction of potentially reparative cells in the valley dosage areas . . . but not smaller than necessary for optimal peak-dose damage to the malignancy, since a nadir valley dose is roughly arithmetically proportional to the arithmetic average of the pair of doses in the adjacent peaks.

A division of a radiation beam into microbeams and the use of a patient-exposure plan that provides non-overlapping beams in the tissue surrounding the target tumor allows the non-target tissue to recover from the radiation injury, in particular by migration of regenerating endothelial and other reparative cells of the small blood vessels to the areas in which the endothelial cells have been injured beyond recovery. Therefore, the probability of radiation-induced coagulative necrosis in normal, non-targeted tissue is lowered, which may improve the effectiveness of clinical radiation therapy for deep-seated and/or superficially situated tumors.

Various studies have shown the microbeam tissue-sparing effect for X-ray microbeams. Although other methods and processes are known for radiation therapy, none provides a method for performing radiation therapy while avoiding significant radiation-induced damage to tissues proximal to, distal to, and interspersed with the targeted lesion.

Present radiation therapies often take many days and weeks of treatment to provide enough radiation to a target tumor. On the other hand, MBRS can provide an effectual treatment in single visit. Very high (or lesser but sufficiently high-) energy radiation may be used with MBRS that results in the destruction of tumor tissue while allowing for the regeneration of healthy tissue adversely affected by the microbeams.

Further, MBRS provides a method for treating cancerous tumors by using extremely narrow, quasi-parallel X-ray microbeams increasing the precision and accuracy of radiation therapy. MBRS also provides a method of using extremely small microbeams of radiation to unexpectedly produce effective radiation therapy while avoiding significant radiation-induced damage to non-targeted tissues.

A major benefit of MBRS is that the microbeams are so narrow that the vasculature of the tissue and other components of the tissue through which the microbeams pass can repair themselves by the infiltration of endothelial cells and other cells from surrounding unirradiated tissue. Present knowledge indicates that such infiltration can take place only over distances on the order of less than 500 µm, that specific distance depending on the specific kind of tissue being irradiated. The dimensions of the microbeams and the configuration of the microbeam array are therefore determinable with reference to the susceptibility to irradiation of the target tissue and the surrounding tissue to irradiation and the capacities of the various involved tissues to regenerate.

U.S. Pat. No. 5,339,247 to Slatkin et al. titled Method for Microbeam Radiation Therapy provides background related to MBRS, and is hereby incorporated by reference for all purposes as if fully set forth herein.

SUMMARY

Accordingly, there is a need for improved radiation therapies that can quickly yet safely treat patients. Further there is a need to focus radiation doses in desired peak dosage regions while minimizing radiation doses in desired valley dosage regions. Further, there remain a need to three-dimensionally shape the MBRS radiation profile to fit the treatment area and to thereby reduce damage to adjacent healthy tissue.

A brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in the later sections.

Various embodiments may also relate to a method of performing microbeam radiation therapy for a subject, including: producing a high-energy radiation beam; shaping, attenuating, and increasing the penetration of the high-energy radiation beam using a low-atomic-weight (i.e., a low-Z) filter; passing the shaped and attenuated beam through a collimator to produce high-dose regions transversely alternating with low-dose regions; and irradiating the tumor-bearing part of the subject with the shaped, attenuated, and collimated beam.

Various embodiments may also relate to a method of performing microbeam radiation therapy for a subject, including: producing a high-energy radiation fan beam, wherein the width of the fan beam in a first direction is greater than the width of the fan beam in a second direction; and shaping the fan beam; producing a relative movement between the subject and the fan beam to irradiate the subject through a collimator to produce high-dose regions alternating with low-dose regions in the targeted zone of the patient, but not lateral to that intended targeted zone.

Various embodiments may also relate to a microbeam radiation therapy system, including: a high-energy radiation beam; a collimator with slits, wherein the collimator only passes the high-energy radiation fan beam through the slits; and a beam shaper configured to spatially limit and filter the high-energy radiation beam.

BRIEF DESCRIPTION OF THE DRAWINGS

In order to better understand various exemplary embodiments, reference is made to the accompanying drawings wherein.

DETAILED DESCRIPTION

Figure 1:
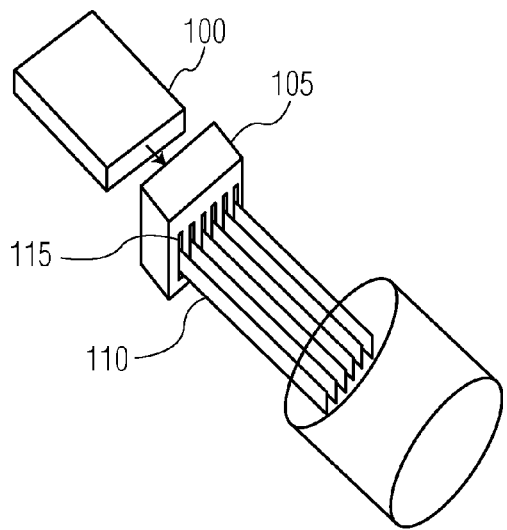
FIG. 1 illustrates a method for producing microbeams using a collimator.

Referring now to the drawings, in which like numerals refer to like components or steps, there are disclosed broad aspects of various exemplary embodiments of our invention.

FIG. 1 illustrates a method for producing microbeams using a collimator. The collimator 105 may include a plurality of parallel slits 115 in a vertical direction. A high-energy radiation fan beam 100 that may be very narrow in the vertical direction and wide in the horizontal direction may pass through the collimator 105. Because the collimator 105 is made of a high Z material, it blocks portions of the of the high-energy radiation fan beam 100. The portion of the high-energy radiation fan beam 100 that passes through the slits 115 of the collimator 105 forms the microbeams 110. The microbeams 110 may be used to treat a subject. Depending upon the vertical height of the fan beam 100 relative to the size of the treatment region, the subject may have to be moved relative to the microbeams 110 in order to irradiate the whole treatment region. It is not possible to move the high-energy radiation fan beam 100 because of the massive size of the facility necessary to produce the high-energy radiation fan beam 100. Further, the collimator 105 has been fixed relative to the high-energy fan beam 100.

MBRS may apply very high-energy radiation beams for a very short period of time. One problem with MBRS may occur when the subject moves relative to the beam during treatment. This may result in smearing of the peak and valley doses applied to the subject. Effective and safe MBRS relies upon valley dose regions where the radiation dose is low enough to prevent any damage to the healthy cells in the valley dose regions. If the subject moves relative to the microbeams 110 during treatment, then the high-energy radiation of the microbeams 110 may smear into the valley-dose regions resulting in many if not all of the healthy cells along the path of the microbeams 110 being injured beyond recovery. Accordingly there is a need to stabilize and fix the microbeams 110 relative to the subject.

The microbeams 110 may be fixed relative to the subject by affixing a collimator to the subject that splits a high-energy fan beam 100 into microbeams 110. In this embodiment, even though the subject may move relative to the high-energy fan beam 100, the collimator moves with the subject, hence the microbeams 115 emanating from the collimator move with the subject as well. This embodiment may prevent the problem described above. Moreover, it permits use of dose rates that are lower than those thought and recorded as feasible to date, thereby allowing use of radiation-generating facilities less costly than those conceived possible to date, which renders this invention distinctly and obviously different in a clinically advantageous manner over previously disclosed treatments.

Figure 2:
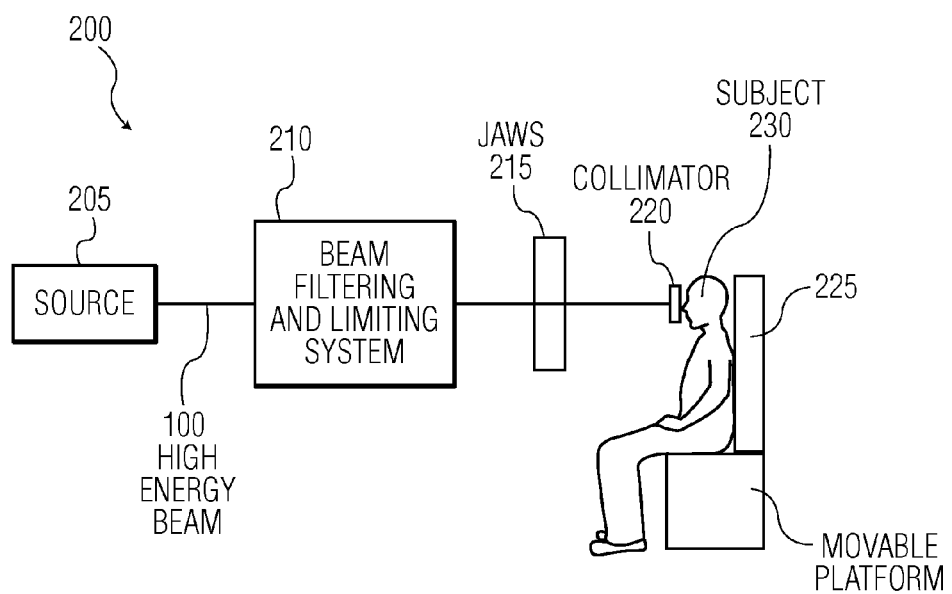
FIG. 2 illustrates an embodiment of a MBRS system.

FIG. 2 illustrates an embodiment of a MBRS system. The MBRS system 200 may include a source 205 that produces a high-energy fan beam 100, a beam filtering and limiting system 210, jaws 215, a collimator 220, and a movable platform 225. A subject 230 may be treated by the MBRS system 200, but not necessarily so.

The source 200 may produce a high-energy electromagnetic radiation beam such as a X-ray or gamma radiation beam. High-energy X-ray radiation may be especially beneficial. In any generated photon beam, the photons are produced having a characteristic spectrum of energies. The photon energy of the beams may optimally range from about 30 keV to about 300 keV, but unlikely optimally outside that range.

A synchrotron may be used to generate an X-ray beam having practically no divergence and a very high fluence rate. These synchrotron generated X-rays have the potential for projecting sharply defined beam edges deep in the body. This source may be useful for generating X-ray microbeams for radiobiology, radiotherapy, and radiosurgery. A high fluence rate may be required to implement MBRS because exposure times must be short enough (e.g., less than about 1 second) to avoid the blurring of margins of the irradiated zones of tissue due to body or organ movements, but not necessarily so if the collimator is affixed to the patient. Even absent such affixation, sharply defined microbeam margins are enabled despite patient movement not only by a high fluence rate and the minimal divergence of the synchrotron beam, but also by the microscopically short ranges in tissue of secondary electrons generated especially by 50-150 keV synchrotron X-rays. Absorbed doses to nontargeted tissues situated between microbeams may be kept below the threshold for radiation damage in tissues both proximal and distal to the isocentric target, i.e., where the microbeams do not overlap. These factors make it possible to effectively irradiate a target using a field of many well-defined, closely spaced microbeams.

The radiation beam for producing the microbeam array may be obtained from industrial X-ray generators or from synchrotron beamlines at electron storage rings. The radiation beam may be obtained from a wiggler beam line at an electron storage ring. A conventional "planar" wiggler uses periodic transverse magnetic fields to produce a beam with a rectangular cross-section, typically having a horizontal-to-vertical beam opening angle ratio on the order of 50:1. In an alternative embodiment, the radiation beam is obtained from a "helical" wiggler, a configuration capable of producing a substantially less anisotropic beam. While a fan beam is discussed in the embodiment below, it is also possible to place the subject to be treated a large distance (e.g., 100 m) from the source 200, which may allow the X-ray beam from the source to expand enough in both the horizontal and vertical directions so that the beam covers the whole treatment region, and hence, it may not be necessary to move the subject relative to the high-energy beam. Further, such beam-spreading could be accomplished by two orthogonal wigglers that would spread the beam first in one direction and then in a second orthogonal direction. Such embodiments would not require movement of the subject, but the collimator would still be affixed to the subject as with the previously described embodiments.

The beam-filtering and beam-limiting system 210 (which may also be designated a beam shaper) filters and limits the high-energy beam 100 for treating the subject 230. As mentioned above the source may produce a high-energy beam with a range of energies. Often only a certain range of energies may be used to treat the subject. Accordingly, various filters made of various materials may be placed in the path of the high-energy beam to filter out the undesired energy bands in the high-energy beam. Further, spatial limiting may be used to limit the beam to the desired beam size and geometry. This may help to prevent unwanted and unsafe stray radiation from the source 200. Such spatial limiting may be accomplished, for example, with plates having slits. The plates may be of sufficient thickness and high-Z material to block portions of the high-energy beam from the source 200.

Jaws 215 further spatially limit the high-energy beam 100 that has passed though the filtering and limiting system 210. The jaws 215 include two jaws that may be made of a material that completely blocks the high-energy beam 100. Because the width of the high-energy fan beam typically may be wider than that of the target region, it may be necessary to limit the width of the fan beam to the width of the target region. Thus, as the subject 230 moves relative to the high-energy fan beam 100, the width of the target region varies. Accordingly, the jaws 215 move to adjust the width of the high-energy fan beam 100 to correspond to the width of the target region being irradiated by the high-energy fan beam 100. Prior to the subject being treated using MBRS, the target region is very accurately measured, so that during treatment with the high-energy fan beam 100, the width of the beam can be adjusted to correspond the precise desired treatment region. This may prevent the unnecessary irradiation of normal healthy tissue adjacent to the treatment region.

With modern diagnostic technology, the boundaries and composition of tumors and other tissues to be treated using MBRS may be very accurately measured. The further discussion below discusses treating tumors, but such description is also intended to include the treatment of any desired tissue. With such an accurate three-dimensional ("3-D") view of the desired treatment area, the shape of the MBRS radiation profile may be modified in three dimensions in order to more accurately treat just the desired treatment area corresponding to the tumor. Such shaping can be done first in a two-dimensional plane perpendicular to the direction of the high-energy radiation. The two-dimensional boundary of the treatment region may be determined based upon the measurement of the tumor. Accordingly, the two-dimensional profile of the treatment region and hence the portion of the high-energy beam that reaches the subject may be varied using various methods and apparatus as described below. Second, the MBRS radiation profile may be varied in a direction parallel to the high-energy beam using various methods and apparatus as describe below. As a result, a three-dimensional radiation profile may be achieved that matches the tumor in order to provide a more accurate treatment of the tumor and less damage to tissue adjacent to the tumor.

Figure 9:
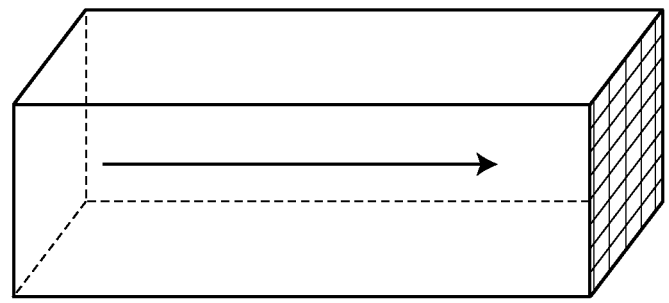
FIG. 9 illustrates a three-dimensional radiation profile that may result using just the collimator.
Figure 10:
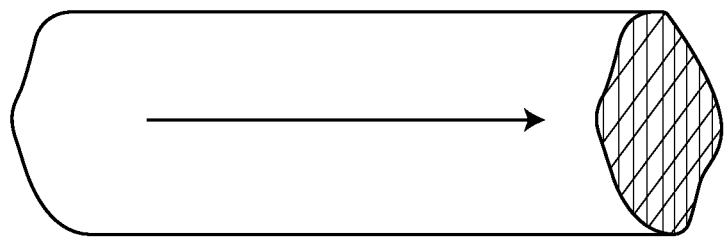
FIG. 10 illustrates a three-dimensional radiation profile that may result using a beam filtering and limiting system.
Figure 11:
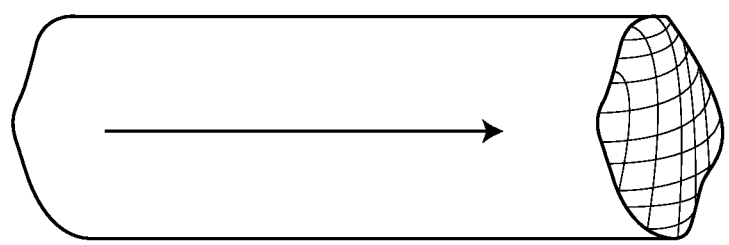
FIG. 11 illustrates another three-dimensional radiation profile that may result using a beam filtering and limiting system.

FIGS. 9-11 may be used to demonstrate the three-dimensional shaping of the high-energy beam. FIG. 9 illustrates a three-dimensional radiation profile that may result using just the collimator 220. The two-dimensional profile of the beam is square and the radiation profile in the direction of the radiation is uniform across the two-dimensional profile. FIG. 10 illustrates a three-dimensional radiation profile that may result using a beam-filtering and beam-limiting system 210. The two-dimensional profile of the beam is shaped to match the shape of the tumor and the radiation profile in the direction of the radiation is uniform across the two-dimensional profile. FIG. 11 illustrates a three-dimensional radiation profile that may result using a beam filtering and limiting system 210. The two-dimensional profile of the beam is shaped to match the shape of the tumor and the radiation profile in the direction of the radiation intensity or spectrum varies across the two-dimensional profile to match the shape of the tumor.

Once the tumor is measured, spatial information regarding the location of the tumor may be provided to a radiation profile analysis system. The measurement data may also include spatial information relating to the specific composition of the tumor at various points in space. For example, the density of the tumor or specific composition of the tumor may be determined at various points in space. Alternatively, it may be assumed that the tumor has a uniform composition. The radiation profile analysis system may use the spatial information and, if available, the composition information, to determine radiation profile to treat the tumor. Such analysis may account for the specific interaction between the radiation source and the tumor. For example, the overall power profile of the high-energy beam may be varied. In addition, the high-energy beam may have an energy spectrum profile. This energy spectrum of the high-energy beam may be varied as well based upon the composition of the tumor to be treated based upon the effectiveness of certain portions of the high-energy spectrum in treating the tumor. The energy spectrum can be set by properties of the wiggler or low-Z filter in the beam.

The radiation profile analysis system may produce a three-dimensional high-energy beam profile to treat the tumor. The profile may include two components. A first component would be the two-dimensional profile in a plane perpendicular to the high-energy beam. This two-dimensional profile may be used as described below. A second component may be a depth profile that varies across the two-dimensional profile of the first component.

Another factor that may affect the treatment of the tumor is the composition of the intermediate tissue between the skin and the tumor that is in the path of the high-energy beam. While measuring the tumor the intermediate tissue may be measured including the composition of the intermediate tissue. As this intermediate tissue may not be uniform it may have an effect on the high-energy beam as it impinges on the tumor. Such affects may be taken into account in determining the radiation profile used to treat the tumor. Such effects would affect the second component or depth profile of the radiation profile.

A first method to produce the two-dimensional profile in a plane perpendicular to the high-energy beam is now described. The two jaws 215 may be independently controlled so as to adjust the location of edges of the high-energy fan beam 100 so that the edges coincide with the edges of the treatment region. This may be based upon the two-dimensional component of the radiation profile. Further, actuators that move the jaws 215 may be able to move the jaws 215 quickly enough to adjust the width of the high-energy fan beam 100. The movement of the jaws may be actuated by a controller that receives information relating to the shape and location of the treatment region. Further, the controller may include a processor for actuating the movement of the jaws 215. Further, while the jaws 215 are shown as spatially independent from the collimator 220, it is also possible that the jaws 215 may be connected to the collimator or the patient so that it moves with the patient as well.

Jaws that provide for a varying width of the high-energy fan beam may also be used in systems where the collimator is not fixed to the patient. For example the collimator may be fixed and stationary and the high-energy fan beam is moved relative to the collimator. Also, in another embodiment, the collimator may be attached to a collimator control apparatus that may move the collimator in any direction relative to the high-energy fan beam. In this embodiment, the collimator may be in unison with the subject or may move relative to the subject. In any of these embodiments, the jaws 225 may be placed anywhere along the path of the high-energy fan beam in order to conform the width of the high-energy fan beam to the desired treatment area of the subject.

Figure 12:
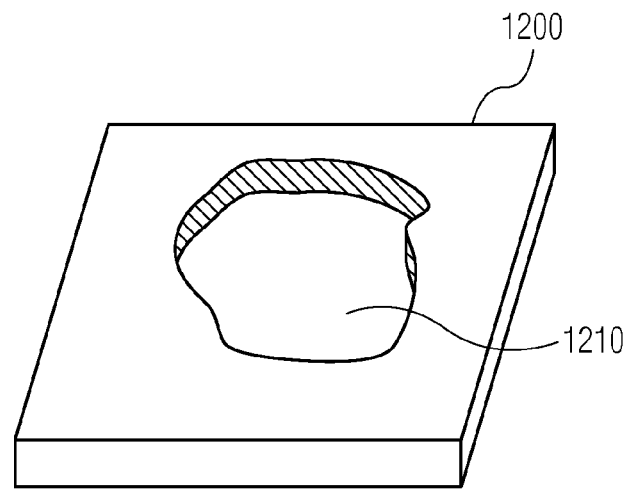
FIG. 12 illustrates a filter plate with an opening in the shape of the two-dimensional component of the radiation profile.
Figure 13:
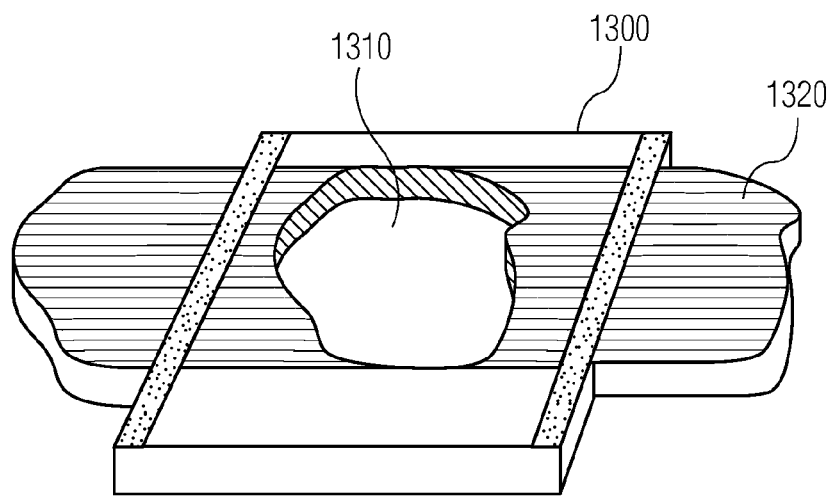
FIG. 13 illustrates a filter plate that includes a plurality of slidable, radio-opaque leafs that may be stacked and adjusted to conveniently and rapidly form any opening corresponding to the desired two-dimensional profile even during the clinical exposure to microbeams if expedient to do so.

Other methods may be used to produce the two-dimensional component of the radiation profile. For example, FIG. 12 illustrates a filter plate 1200 with an opening 1210 in the shape of the two-dimensional component of the radiation profile. Such a filter plate may be made of a material that blocks the high-energy beam. Alternatively, as shown in FIG. 13, the filter plate 1300 may include a plurality of slidable leafs 1320 that may be stacked and adjusted to form any opening corresponding to the desired two-dimensional profile. These filter plates 1200, 1300 may also be placed at various places along the path of the high-energy beam in order to provide two-dimensional shaping of the high-energy beam.

The depth profile for the radiation profile may be implemented in various ways. First as the high-energy beam scans across the subject, the intensity of the high-energy beam may be varied. This may be done by rapidly varying components of the device that emits the high-energy beam. Alternatively, a rapidly variable beam attenuator may be placed along the path of the high-energy beam and controlled according to the depth profile. In this embodiment, the high-energy beam fans out in first direction while the high-energy beam scans (or is scanned) in a second direction perpendicular to the first direction. Accordingly the intensity of the radiation applied along the first direction is constant, while the intensity of the radiation applied along the second direction (i.e., the scanning direction) may vary. The variation of the intensity of the high-energy beam may be controlled based upon the depth profile. At a given point along the scanning direction of the high-energy beam, the depth profile along the first direction at the given point is determined, and the highest intensity required may be used for the high-energy beam at that point. This provides the needed radiation along the region radiated by the high-energy beam at the given point. While this method does not provide a complete two-dimensional variation of the depth profile, this method does reduce the overall radiation applied to the subject and thus reduces the potential damage to tissue adjacent to the tumor.

Also, a two-dimensional beam profile may be implemented by using filters that alter the high-energy beam intensity profile. Such filters may be made of radiation-opaque materials of varying thicknesses in order to achieve the desired high-energy beam intensity profile that corresponds to the desired depth profile. Such filters may be plates that are machined from high Z materials to shape the high-energy beam intensity profile. Such filters may also be formed using three-dimensional printing techniques or various metal deposition techniques. Such filters may also include layers of different materials with different Z values. For example, a plate made of a laminate of multiple different materials may be machined to achieve the desired shape and profile. Such filters may be machined on two sides to allow for greater control of the final filter intensity profile. Alternatively, different materials may be used in the three-dimensional printing or deposition methods. The use of various materials with different Z values allows for fine-tuning of the filter intensity profile. For example, a low-Z material may be used in order to achieve a more precise over all Z value, thus leading to a more accurate filter intensity profile within the mechanical tolerances of the methods used to form the filter. Further, the materials selected may be used to filter the frequency spectrum of the radiation. Such narrowing of the frequency spectrum or the selection of specific portions of the frequency spectrum may be done according to the tumor being treated as well as to the sensitivity to various types of radiation of adjacent tissue.

Further, the filtering may be done using the collimator. The collimator may be formed having slits that have varying lengths across the treatment region that conform to the shape of the tumor. Further, the slits may be filled with materials that attenuate the high-energy beam passing through the slits. Such attenuations may create a radiation profile matching the shape of the tumor to be treated.

The shaped high-energy fan beam 100 may irradiate the collimator 220. As described above with respect to the FIG. 1, the collimator 220 may include a plurality of vertical slits. The vertical slits split the high-energy fan beam 100 into a plurality of microbeams 110 (as shown in FIG. 1). The collimator 220 may be affixed securely to the subject. Preferably, the collimator 220 is very near the subject 230 or even in contact with the skin of the subject 230. As a result, the microbeams formed by the collimator 220 are fixed relative to the subject, even if the subject moves.

Figure 3:
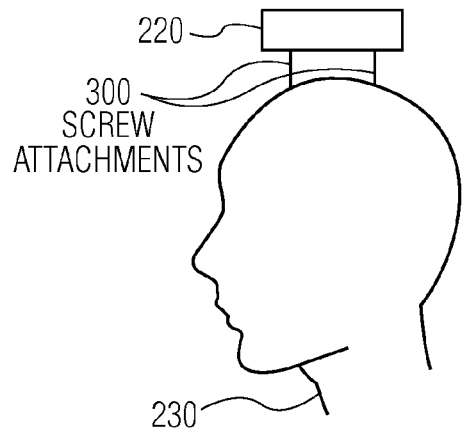
FIG. 3 illustrates affixing a collimator to the skeleton of a subject.

The collimator 220 may be fixed to the skeleton of the subject 220 as shown in FIG. 3. The collimator 220 may be attached to the subject 230 using screws 300 or another fastener 300 that may be used to affix items to the skeleton. The collimator may be affixed to the skull as shown in FIG. 3, but may also be affixed, for example, to the skull, the hip, the spine, the clavicle, or to bones in the arm or the leg.

Figure 4:
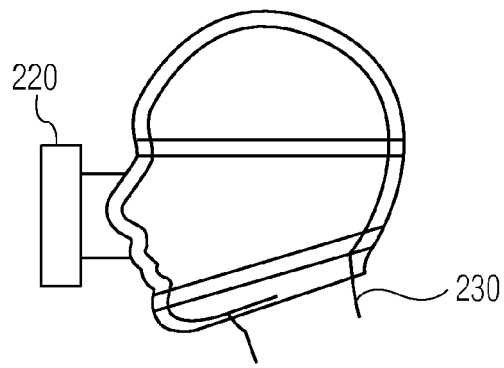
FIG. 4 illustrates affixing a collimator to a subject using a facial mask.

The collimator 220 may also be affixed to the subject 230 using a facial mask 400 as shown in FIG. 4. A facial mask 400 may be placed over the face of the subject 230 and held in place using straps or any other secure method. Then the collimator 220 may be attached to the mask 400.

Further, the collimator 220 may be affixed to the subject 230 by clamping the collimator 220 or a related fixture between the upper and lower jaws of the subject. The subject's jaws may then be held in place using straps or some other method.

Also, a fixture may be used to help affix the collimator 220 to the subject 230. The fixture may be attached to the face, skeleton, jaw or other stable part of the subject. Then the collimator 220 may be attached to the fixture.

It is important to precisely and accurately affix the collimator 220 relative to the target region in the subject 230 that is to be treated. This may be accomplished by affixing the collimator or the fixture to the subject 230 in the desired location. Then a diagnostic test may be performed to verify the alignment of the collimator 230 or fixture with the treatment region. Then the location of the collimator 230 or the fixture may be adjusted, and the diagnostic test repeated. This process may be repeated as many times as needed to achieve the desired alignment accuracy between the collimator 220 and the target region of the subject 230.

The movable platform 225 may hold the subject in a fixed position and then move the subject relative to the high-energy fan beam 100. The movable platform 225 may be any known platform that secures the patient and then allows for precise and accurate movement of the patient relative to the high-energy fan beam 100.

Further, the MBRS may be conducted in order to accommodate tissue movement in the subject due to the cardiac or respiratory cycle. The exposure interval of the high-energy beam 100 may be synchronized with either the cardiac or the respiratory cycle or both. Each exposure interval may be limited to a small time interval during the appropriate cycle to avoid the smearing of the extraordinarily precise microbeam effect by movement of the tissue generated by cardiogenic and respiratory pulsation. For example, the exposure interval of the high-energy beam 100 may be limited to the end phase of diastole or the end phase of an exhalation cycle. Other predicable points of these cycles may be used as well. In yet another embodiment, the diagnostic tests performed to characterize the target region or to align the collimator with the target region may be carried out at specific predetermined portion of the cardiac or respiratory cycle. Then the exposure interval of the high-energy beam 100 may be during the same specific predetermined portion of the cardiac or respiratory cycle, and may include one or more exposure interval periods. The use of compensation for the cardiac and respiratory cycle may depend on the target regions susceptibility to movement due to these cycles.

Because such high-energy radiation may be used in MBRS it is very important to precisely control the dose of radiation applied to the subject 230, prior to treatment, a medical physicist may use sophisticated computer tools and modeling to determine the dosage parameters to use during the MBRS. In order to evaluate the MBRS dosage radiobiologically in addition to physically, a two-dimensional array of microscopic cell-culture chambers may be used. The array may be placed downstream from the collimator 220 in close proximity to or in contact with the subject's skin. Those cells behind the radiolucent slits and their similar but minimally irradiated cells in the same two-dimensional array behind the radioopaque bars of the collimator between its radiolucent slits would indicate, with nearly cell-by-cell spatial resolution, the biologically effective dose received by the skin cells, which are important reference doses for computation by the medical physicist of valley doses in radiosensitive vital normal tissues deep to the skin, proximal and distal to the target region, outlined in diagnostic tests. Such a two-dimensional array may also be placed near the collimator 220 without a subject and irradiated to determine the radiobiological effects of a proposed treatment dosage.

While the application of a single MBRS dose may be effective to treat a subject, it may also be beneficial to provide multiple treatments from different directions, i.e., stereotactically. The treatment directions and doses would be selected to allow the two different sets of microbeams to intersect in the target region. These multiple doses of high-energy radiation to the treatment region may increase the effectiveness of the MBRS for a lesion.

While the high radiation beam 100 is described as being spread in the horizontal direction, it may be beneficial to spread the beam in the vertical direction or any other direction. Using other beam spreading directions may provide benefits in accurately delivering a dose. Also, if multiple MBRS treatments are used, then the ability to spread the high-energy beam 100 in various directions may be beneficial. For example, when producing high-energy X-rays using a synchrotron, a wiggler may be used to spread the beam in a desired direction. Such a wiggler may be mounted so that it can be rotated around an axis parallel to the high-energy beam. As a result the beam may be spread in any desired direction. The rotation of the wiggler may be precisely and accurately controlled to allow the beam to spread as needed to apply the desired radiation dose.

Prior research, has shown that "blanching" (i.e., temporarily restricting blood flow to) the subject's skin during exposure to photonic ionizing radiation reduces the damage done to the skin. Accordingly, this benefit may be combined with the treatment method and system according the present embodiments. Blanching of the skin may be accomplished by applying pressure to the skin irradiated by the microbeams 110. Such pressure may be applied by a tightly applied bandage or band. Further, pressure may be applied to the skin by using a gas-filled elastic bladder placed between the skin of the subject and the collimator 220. Another method of blanching the skin includes injecting adrenaline into an area near the skin to be blanched. Any other method to blanch the skin, hitherto known or hitherto unknown, may be used, alternatively or concomitantly.

Figure 5:
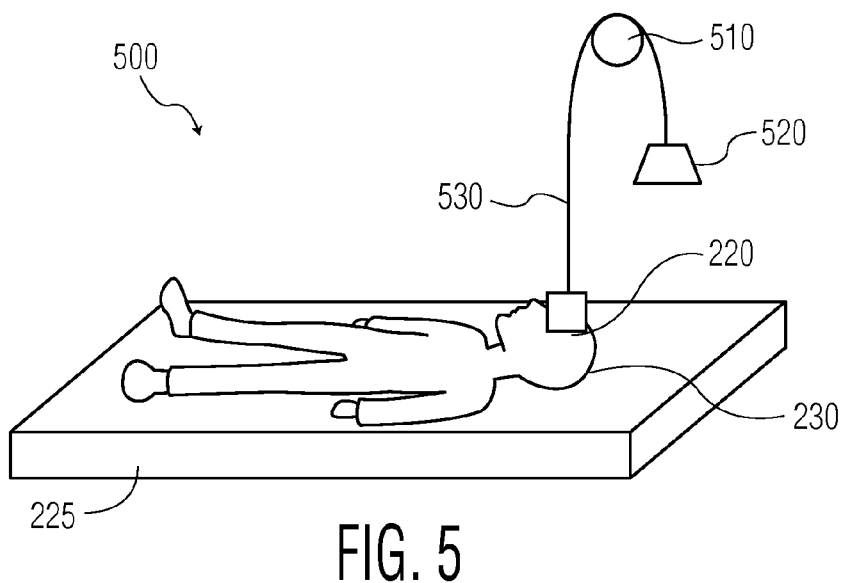
FIG. 5 illustrates a pulley system that may help to counter the weight of the collimator.

Because the collimator 220 may be heavy because of its size and the use of dense materials needed to block the high-energy radiation beam 200, it may be uncomfortable to the subject to support the weight of the collimator 220. Accordingly, this weight may be offset using a pulley or lever arm system. FIG. 5 illustrates a pulley system 500 that may help to counter the weight of the collimator 230. The pulley system 500 may include a pulley 510, a counter-weight 520, and a cable 530. The cable 530 may attach to the collimator 220 and then extend through and over pulley 510 and then attach to the counter-weight 520. The counter-weight 520 is approximately the same weight as the collimator 220, so that the effective weight of the collimator 220 on the subject is nearly zero. Further, the pulley may be subject to a small frictional force to minimize the movement of the pulley except when a sufficient force is applied to the cable 530.

Figure 6:
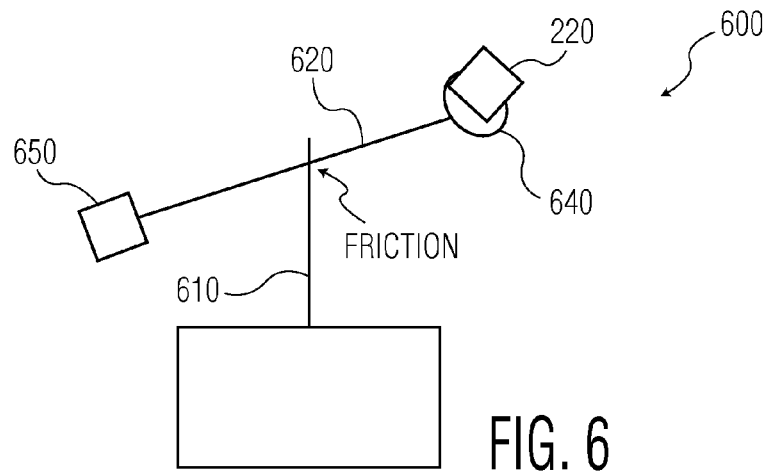
FIG. 6 illustrates another embodiment of a system to counter the weight of the collimator.

FIG. 6 illustrates another embodiment of a system 600 to counter the weight of the collimator 230. The lever system 600 may include a base 610, a lever arm 620, a counter-weight 630, and a gimbal 640. The base 610 supports the lever arm 620 and allows the lever arm 620 to pivot about a connection point between the base 610 and the lever arm 620. A counter-weight 630 is attached to one end of the lever arm 630 to counterbalance weight at the gimbal end of the lever arm 630. The weight of the counter-weight 630 may be selected in order to counter the weight of the collimator 220. The collimator 220 may be attached to a gimbal 640 at the end of the lever arm 620 opposite the counter-weight 630. The gimbal allows the collimator 220 be oriented in any needed direction. Other mechanical systems may be used as well to offset the weight of the collimator 220 in order to prevent or alleviate transient discomfort to the subject.

As described above with respect to FIG. 1, the collimator 105 may include alternating radiation-translucent regions and radiation-opaque regions. The radiation-translucent regions may be slits 115 formed in a radiation-opaque material. Also, the radiation-translucent region may be made of a radiation-translucent material that allows the high-energy beam 100 to pass through the collimator 105 to form the microbeams 110.

Figure 7:
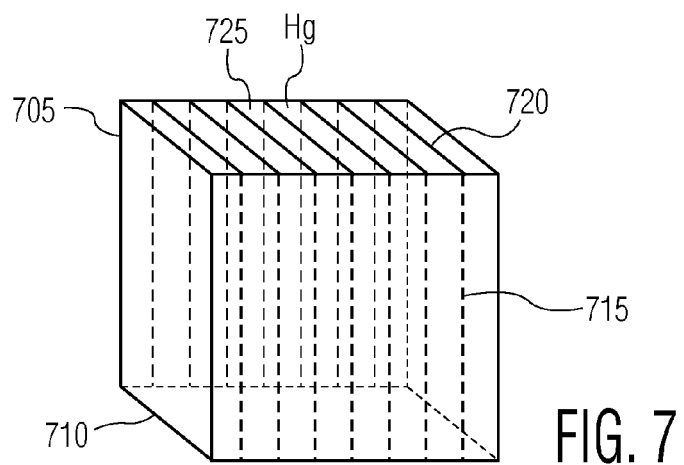
FIG. 7 illustrates one embodiment of a collimator.

FIG. 7 illustrates one embodiment of a collimator. The collimator 705 may include an enclosure 710, radiation-translucent foils 720, and radiation-opaque liquid 725. The enclosure 710 may have two substantially parallel opposite sides with grooves 715. The radiation-translucent foils 720 may be mounted in opposite pairs of grooves 715. All of the radiation-translucent foils 720 may be substantially parallel to each other. The radiation-translucent foils 720 may be made of aluminum or of any other material that is sufficiently radiation-translucent. Next a liquid radiation-opaque material such as mercury maybe added to the regions in between the radiation-translucent foils 720. Such a collimator 705 would allow for the easy construction of various collimators 705 with various parameters, such as foil height, width, and thickness and the spacing between the foils.

Figure 8:
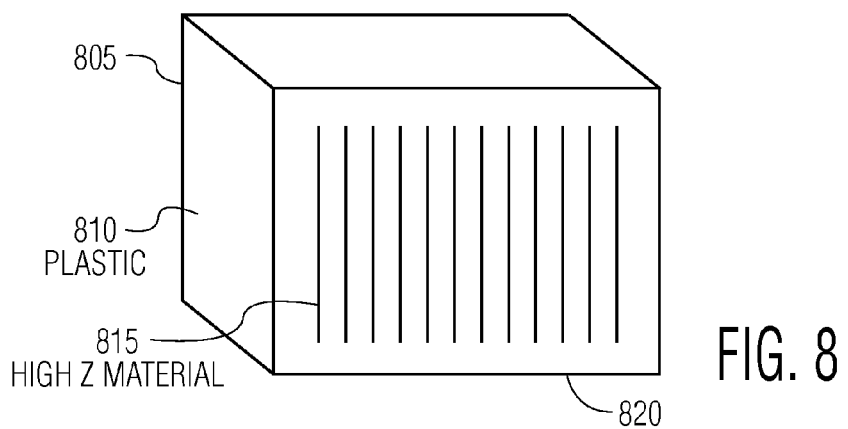
FIG. 8 illustrates another embodiment of a collimator.

FIG. 8 illustrates another embodiment of a collimator. The collimator 805 may include a body 810 and layers 815. The body may be made of a radiation-translucent material such as for example plastic. Plastic has the advantage that it may be easily machined to create slits. The slits may be formed using micromachining techniques. Further, the body 810 may include a machinable side 820. This machinable side may be machined to conform to specific portion of the subject's body. This would allow for accurate, stable, and comfortable placement of the collimator 805 in contact with the subject.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

We claim:

1. A method of performing microbeam radiation therapy for a subject, comprising:
   producing a high-energy radiation fan beam, wherein the width of the fan beam in a first direction is greater than the width of the fan beam in a second direction;
   shaping the fan beam; and
   producing a relative movement between the subject and the fan beam to irradiate the subject through a collimator to produce high-dose regions alternating with low-dose regions,
   wherein the collimator is affixed to the subject.

2. The method of claim 1, wherein shaping the fan beam includes adjusting the width of the fan beam in the first direction while producing a relative movement between the subject and the fan beam in the second direction.

3. The method of claim 2, wherein the width of the fan beam is adjusted to correspond to a desired treatment region in the subject.

4. The method of claim 2, wherein adjusting the width of the fan beam in the first direction includes adjusting the position of a set of adjustable jaws configured to block a portion of the high-energy radiation beam.

5. The method of claim 2, wherein adjusting the width of the fan beam in the first direction includes placing a filter in the path of the fan beam.

6. The method of claim 1, wherein shaping the fan beam includes adjusting the intensity profile of the fan beam.

7. The method of claim 6, wherein a filter is used to adjust the intensity profile of the fan beam.

8. The method of claim 6, wherein the collimator includes a filter that is used to adjust the intensity profile of the fan beam.

9. The method of claim 1, further comprising receiving a radiation treatment profile and wherein shaping the fan beam includes shaping the fan beam based upon the radiation treatment profile.

10. A microbeam radiation therapy system, comprising:
    a high-energy beam source configured to produce a high-energy radiation beam;
    a collimator with slits, wherein the collimator only passes the high-energy radiation beam through the slits, and wherein the collimator is affixed to a subject; and a beam shaper configured to spatially limit and filter the high-energy radiation beam.

11. The system of claim 10, wherein the beam shaper adjusts the shape of the high-energy radiation beam.

12. The system of claim 11, wherein the shape of the high-energy radiation beam is adjusted to correspond to a desired treatment region.

13. The system of claim 11, wherein the high-energy radiation beam is a fan beam and the beam shaper includes a set of adjustable jaws configured to block a portion of the fan beam.

14. The system of claim 11, wherein the beam shaper includes a filter in the path of the high-energy radiation beam.

15. The system of claim 11, wherein the beam shaper is configured to adjust the intensity profile of the high-energy radiation beam.

16. The system of claim 10, wherein the beam shaper is part of the collimator.

17. The system of claim 10, wherein the beam shaper includes a plurality of slidable leafs configured to provide an opening in the beam shaper.

18. The system of claim 10, wherein the beam shaper includes a filter having a spatially varying thickness.

19. The system of claim 10, wherein the high-energy radiation beam is a fan beam and wherein the high-energy beam source varies the peak energy of the fan beam based upon a radiation treatment profile.

20. A method of performing microbeam radiation therapy for a subject, comprising:

producing a high-energy radiation beam;

shaping and attenuating the high-energy radiation beam using a filter;

passing the shaped and attenuated beam through a collimator to produce high-dose regions alternating with low-dose regions; and irradiating the subject with the shaped, attenuated, and collimated beam, wherein the collimator is affixed to the subject.

* * * * *